(12) United States Patent
Kuehner

(10) Patent No.: US 9,388,314 B2
(45) Date of Patent: Jul. 12, 2016

(54) SURFACE MODIFIED SILICON DIOXIDE PARTICLES

(75) Inventor: Uwe Dietrich Kuehner, Hamburg (DE)

(73) Assignee: EVONIK HANSE GMBH, Geesthacht (DE)

( * ) Notice: Subject to any disclaimer, the term of this patent is extended or adjusted under 35 U.S.C. 154(b) by 604 days.

(21) Appl. No.: 12/988,482

(22) PCT Filed: Apr. 20, 2009

(86) PCT No.: PCT/EP2009/002875
§ 371 (c)(1),
(2), (4) Date: Oct. 18, 2010

(87) PCT Pub. No.: WO2009/127438
PCT Pub. Date: Oct. 22, 2009

(65) Prior Publication Data
US 2011/0039983 A1    Feb. 17, 2011

(30) Foreign Application Priority Data

Apr. 18, 2008  (EP) ..................... 08007625

(51) Int. Cl.
| | | |
|---|---|---|
| *C09C 1/30* | (2006.01) | |
| *C07C 51/44* | (2006.01) | |
| *B82Y 30/00* | (2011.01) | |
| *C08K 9/06* | (2006.01) | |

(52) U.S. Cl.
CPC ............... *C09C 1/3081* (2013.01); *B82Y 30/00* (2013.01); *C07C 51/44* (2013.01); *C08K 9/06* (2013.01); *C01P 2004/51* (2013.01); *C01P 2004/54* (2013.01); *C01P 2004/62* (2013.01); *C01P 2004/64* (2013.01); *C01P 2006/22* (2013.01)

(58) Field of Classification Search
CPC ............................. C09C 1/3081; C07C 51/44
See application file for complete search history.

(56) References Cited

U.S. PATENT DOCUMENTS

| | | |
|---|---|---|
| 2,786,042 A | 3/1957 | Iler et al. |
| 2,801,185 A | 7/1957 | Iler et al. |
| 5,889,132 A | 3/1999 | Rheinberger et al. |
| 5,942,590 A | 8/1999 | Burns et al. |
| 6,051,672 A | 4/2000 | Burns et al. |
| 6,107,351 A | 8/2000 | Burns et al. |
| 6,316,155 B1 | 11/2001 | Kudo et al. |
| 6,376,559 B1* | 4/2002 | Komoto et al. ............... 516/34 |
| 6,673,458 B2* | 1/2004 | Mager .................. C08G 77/06 428/402 |
| 6,706,398 B1 | 3/2004 | Revis et al. |
| 6,736,891 B1 | 5/2004 | Bice et al. |
| 2003/0138715 A1 | 7/2003 | Barthel et al. |
| 2004/0052939 A1 | 3/2004 | Boswell et al. |

FOREIGN PATENT DOCUMENTS

| | | |
|---|---|---|
| EP | 0 982 268 A | 3/2000 |
| JP | 2000-80201 | 3/2000 |
| WO | WO 2006114420 A1 * | 11/2006 |

* cited by examiner

*Primary Examiner* — Peter D Mulcahy
(74) *Attorney, Agent, or Firm* — Henry M. Feiereisen LLC; Ursula B. Day

(57) ABSTRACT

Surface-modified silicon dioxide particles or silica sol preparable by reacting aqueous silica sol with at least one first modifier comprising at least one alkoxysilane and with at least one second modifier selected from the group consisting of halosilane, siloxane, and mixtures thereof, with water being removed before the reaction with the first or second modifier.

16 Claims, No Drawings

SURFACE MODIFIED SILICON DIOXIDE PARTICLES

CROSS-REFERENCES TO RELATED APPLICATIONS

This application is the U.S. National Stage of International Application No. PCT/EP2009/002875, filed Apr. 20, 2009, which designated the United States and has been published as International Publication No. WO 2009/127438 and which claims the priority of European Patent Application, Ser. No. 08 007 625.0, filed Apr. 18, 2008, pursuant to 35 U.S.C. 119(a)-(d).

BACKGROUND OF THE INVENTION

The present invention relates to modified silicon dioxide particles, and also to a process for preparing modified silicon dioxide particles and to the products obtainable by that process, to particular end uses of the silicon dioxide particles, and to nanocomposites which comprise the silicon dioxide particles. Also proposed are silica sols comprising the modified silicon dioxide particles.

Silica sol is a suspension of amorphous silicon dioxide ($SiO_2$) in which the silicon dioxide is present in the form of spherical individual particles which are substantially (i.e., to an extent of at least 50%, preferably to an extent of at least 70%, 80% or 90%) noncrosslinked with one another. The dispersion medium may be different—thus, for example, a solvent or a monomer.

Silica sols are widely used. For example, they are suitable for use as binders for precision casting, for fibers in the refractories sector, and in the production of catalysts, as coating agents for films (antiblocking), in the textile segment for nonslip finishes, in the construction sector as additives for air-placed concrete, or as binders for fire protection and thermal insulation applications, as polishing agents for electronics or else in the paper segment, in the context, for example, of paper retention or as an additive in the coating of speciality papers.

Conventional silica sols, depending on the size of the silicon dioxide particles, are milkily cloudy through opalescent to colorlessly clear in form. The particles generally have diameters of 5 nm to 150 nm and are usually spherical, three-dimensionally limited, and preferably negatively charged electrically. In the interior of the individual particles there is typically a framework of siloxane compounds which is a result of the linking of [$SiO_4$] tetrahedra and/or of polysilicic acids.

In view of their small size, the particles have a large specific surface area, leading in turn to a high surface energy. One unwanted consequence of this high surface energy is that the particles tend to form agglomerates or even aggregates. Forming stable dispersions comprising silicon dioxide particles is therefore not readily possible.

In order as far as possible to prevent the agglomeration or aggregation of the particles, it is known from the prior art to modify them on their surface.

Thus "The Chemistry of Silica" by Ralph K. Iler (1979. John Wiley & Sons, Inc.; New York, Chichester, Brisbane, Toronto) discloses modifying silicate surfaces with chlorosilanes.

EP 0 982 268 A describes the reaction of aqueous silica sols in the presence of water-miscible solvents with halosilanes and mixtures of siloxanes and halosilanes and/or siloxanes.

U.S. Pat. No. 6,736,891 describes the reaction of an aqueous suspension of precipitated silicas at a low pH with hexamethyldisiloxane in the presence of isopropanol.

The flexibility of the modified silicon dioxide particles and their preparation processes, known from the prior art, is inadequate. For instance, the possibilities of adapting the particles for further processing to composites are limited.

U.S. Pat. No. 2,801,185 discloses an organic, surface-modified silicon dioxide particle and also a process for preparing it, in which a water-comprising silica sol is admixed with an organic solvent and the water is removed azeotropically, the water fraction thus being lowered to below 1%. Subsequently a modifier (coating material) is added and the modification of the surface is performed. Coating materials mentioned include saturated primary and secondary alcohols. A disadvantage of these particles, however, is that they do not have the desired stability and/or in some cases do not allow the desired flexibility in further processing.

From U.S. Pat. No. 2,786,042 it is known to modify organic silica sols with hydrocarbon-containing silanols on the surface.

A disadvantage of these known processes, accordingly, is that they result in modified particles of only limited redispersibility. Furthermore, their compatibility with organic solvents, such as toluene and hexane, or with organic resins and polymers, is restricted. Furthermore, the particles can be modified only within narrow limits, and so a flexible adaptation is not possible.

SUMMARY OF THE INVENTION

The object of the present invention lies, therefore, in the provision of surface-modified silica sol particles (silicon dioxide particles) which exhibit improved redispersibility or enhanced compatibility in certain organic solvents, particularly in toluene.

This object is achieved by silicon dioxide particles whose surface has been modified by a degree of coverage as follows:
 a. 0.1 to 16 groups/$nm^2$ of the kind (modification of type A) (surface-SiO)$_x$—Si(R$^1$)$_y$(OR$^2$)$_{4-x-y}$
 where x=1 to 3. y=1 to 3 and x+y=2 or 3; and
 b. 0.1 to 16 groups/$nm^2$ of the kind (modification of type B) (surface-SiO)$_z$SiR$^3_{4-z}$
 where z=1 or 2;
 and where the radicals R$^1$, R$^2$, and R$^3$ can represent any desired organic radicals, and two or more radicals R$^1$, R$^2$ or R$^3$ may be identical or different.

In accordance with the invention it has been found that the particles modified on the surface in this way exhibit outstanding redispersibility in organic solvents and outstanding compatibility with solvents, such as toluene. The primary reason for this is that their surface, by virtue of the above-described modification, has been provided with organic radicals. Critical to this is that the particles actually have the two inventively different modifications A and B. The invention, accordingly, does not embrace variants in which the modification of type A is the same as the modification of type B. The modification of type A is therefore not the same as the modification of type B (A≠B).

The silicon dioxide particles of the invention have a modification of the kind (surface-SiO)$_x$—Si(R)$_y$(OR)$_{4-x-y}$ (modification kind of type A) of preferably 0.1 to 16. preferably 0.1 to 10 groups/$nm^2$, in particular 0.15 to 6 groups/$nm^2$, very preferably 0.2 to 4 groups/$nm^2$.

Additionally they have a modification of the kind (surface-SiO)$_z$—SiR$^3_{4-z}$, (modification kind of type B) of 0.1 to 16.

preferably 0.2 to 10 groups/nm², in particular 0.3 to 6 groups/nm², more preferably 0.4 to 4 groups/nm².

The above-stated preference ranges for modification kinds of type A and B may be combined arbitrarily with one another. The specific combination is dependent on the necessities of the wider use areas and the further processing of the particles. Preference is given to a combination of in particular 0.9-3.6 groups/nm² of the modification of type A and 0.5-3 groups/nm² of the modification of type B.

The skilled worker is aware of methods for determining functional groups on the surface of the particles, and hence also the coverage of the particles of the invention. For instance, groups can be cleaved off from R$_2$Si and R$_3$Si by means of bases (e.g., potassium hydroxide), and then form disiloxanes (R$_3$SiOSiR$_3$) or rings (R$_2$SiO)n. These species can be analyzed by GC. The method is mentioned, for example, in EP 0982268 B1 (comparative example and example 1). The groups can also be determined in principle by NMR and IR. Vinyl groups, furthermore, may be detected by titrimetry via the iodine number, namely through the reaction of the vinyl groups with Wijs solution and subsequent titration of the excess halogen with sodium thiosulfate. (Meth)acryloyl groups can be determined by differential scanning calorimetry (DSC) in the course of reaction with standardized peroxide solutions, from the heat of reaction that is liberated.

Modification of Type A

The modification of the particle surface of type A is accomplished by reacting silica sols with alkoxysilanes of the general formula (I)

$$R^1_xSi(OR^2)_{4-x}, \qquad \text{Formula (I)}$$

in which the radical R$^1$ is an optionally substituted or functionalized C$_1$-C$_{18}$ alkyl radical and the radical R$^2$ may be selected from the group consisting of an optionally substituted or functionalized C$_1$-C$_{18}$ alkyl radical, a carboxyl radical, an optionally substituted C$_2$-C$_{18}$ alkenyl radical, and an oxime radical.

In the context of the present invention, the compounds of the general formula (I) are selected preferably from the group consisting of methyltrimethoxysilane, trimethylmethoxysilane, methylhydrodimethoxysilane, dimethyldimethoxysilane, ethyltrimethoxysilane, ethyltriacetoxysilane, propyltrimethoxysilane, diisopropyldimethoxysilane, diisobutyldimethoxysilane, chloropropyltrimethoxysilane, chloropropylmethyldimethoxysilane, chloroisobutylmethyldimethoxysilane, trifluoropropyltrimethoxysilane, trifluoropropylmethyldimethoxysilane, isobutyltrimethoxysilane, n-butyltrimethoxysilane, n-butylmethyldimethoxysilane, phenyltrimethoxysilane, phenyltrimethoxysilane, phenylmethyldimethoxysilane, triphenylsilanol, n-hexyltrimethoxysilane, n-octyltrimethoxysilane, isooctyltrimethoxysilane, decyltrimethoxysilane, hexadecyltrimethoxysilane, cyclohexylmethyldimethoxysilane, cyclohexylethyldimethoxysilane, dicyclopentyldimethoxysilane, tert-butylethyldimethoxysilane, tert-butylpropyldimethoxysilane, dicyclohexyldimethoxysilane, mercaptopropyltrimethoxysilane, mercaptopropylmethyldimethoxysilane, bis(triethoxysilylpropyl) disulfide, bis(triethoxysilylpropyl) tetrasulfide, aminopropyltrimethoxysilane, m-aminophenyltrimethoxysilane, aminopropylmethyldiethoxysilane, phenylaminopropyltrimethoxysilane, aminoethylaminopropyltrimethoxysilane, aminoethylaminopropylmethyldimethoxysilane, glycidyloxypropyltrimethoxysilane, glycidyloxypropylmethyldimethoxysilane, epoxycyclohexylethyltrimethoxysilane, γ-methacryloyloxypropyltriacetoxysilane, vinyltriacetoxysilane, vinyltrimethoxysilane, methylvinyldimethoxysilane, vinyldimethylmethoxysilane, divinyldimethoxysilane, vinyltris(2-methoxyethoxy)silane, hexenyltrimethoxysilane, γ-methacryloyloxypropyltrimethoxysilane, acryloyloxypropyltrimethoxysilane, vinylbenzylethylenediaminopropyltrimethoxysilane, vinylbenzylethylenediaminopropyltrimethoxysilane hydrochloride, allylethylenediaminepropyltrimethoxysilane, allyltrimethoxysilane, allylmethyldimethoxysilane, allyldimethylmethoxysilane, and hexenyltrimethoxysilane.

Particularly preferred in the context of the present invention are silanes of the general formula (I-1)

$$R^1Si(OR^2)_3 \ (x=3) \qquad \text{Formula (I-1)}$$

where the radicals R$^1$ and R$^2$ are as defined above.

Modification of Type B

The modification of the particle surface of type B is carried out via a reaction with a halosilane and/or a siloxane.

These halosilanes preferably have the general formula (II)

$$R^3_aH_bSiX_{4-a-b} \qquad \text{Formula (II)}$$

in which each R$^3$, independently of any other, is selected from the group consisting of hydrocarbon radicals having 1 to 18 carbon atoms or organofunctional hydrocarbon radicals having 1 to 18 carbon atoms;

X, independently at each occurrence, is selected from the group consisting of fluorine, chlorine, bromine, and iodine;

a is 0, 1, 2 or 3;

b is 0 or 1; and a+b=1, 2 or 3.

Particularly preferred in the context of the present invention are chlorosilanes of the general formula (II-1)

$$R^3_aH_bSiCl_{4-a-b}, \qquad \text{Formula (II-1)}$$

where the radical R$^3$ and the indices a and b are as defined above.

Especially preferred in the context of the present invention are halosilanes of the general formula (II-2)

$$R^3_aH_{3-a}SiCl, \qquad \text{Formula (II-2)}$$

where the radical R$^3$ and the index a are as defined above.

In the context of the present invention, the compounds of the general formula (II) are preferably selected from the group consisting of chlorotrimethylsilane, bromotrimethylsilane, iodotrimethylsilane, dichlorodimethylsilane, dichloromethylsilane, methyltrichlorosilane, chlorodimethylsilane, trichlorosilane, ethyltrichlorosilane, propyltrichlorosilane, phenyltrichlorosilane, dichlorodiphenylsilane, n-hexyltrichlorosilane, n-octyltrichlorosilane, chlorodimethyloctylsilane, chlorodimethyloctadecylsilane, vinyltrichlorosilane, dichloromethylvinylsilane, chorodimethylvinylsilane, dichlorodivinylsilane, γ-methacryloyloxypropyldimethylchlorosilane, allyltrichlorosilane, allyldichloromethylsilane, and allylchlorodimethylsilane.

The siloxanes have the preferred general structure (III)

$$R^3_nSiO_{(4-n)/2} \qquad \text{Formula (III)}$$

in which each R$^3$, independently of any other, is selected from the group consisting of hydrocarbon radicals having 1 to 18 carbon atoms, organofunctional hydrocarbon radicals having 1 to 18 carbon atoms, a hydrogen atom, and an OH group; and n is a number between 2 and 3, inclusively.

Preferred in the context of the present invention are siloxanes of the general formula (III-1)

$$R^3_3SiOSiR^3_3, \qquad \text{Formula (III-1)}$$

where the radical R$^3$ is as defined above, and two or more R$^3$s may each have a different definition.

Further preferred in the context of the present invention are cyclic siloxanes of the general formula (III-2)

$$(R^3{}_2SiO)_n, \quad \text{Formula (III-2)}$$

where n is an integer, and two or more $R^3$s may each have a different definition.

Further preferred in the context of the present invention are polysiloxanes of the general formula (III-3)

$$R^3{}_3SiO(R^3{}_2SiO)_nSiR^3{}_3, \quad \text{Formula (III-3)}$$

where n is an integer, and two or more $R^3$s may each have a different definition.

In one preferred embodiment a polysiloxane of the compound III-1 is used.

In the context of the present invention, the compounds of the general formula (III) are preferably selected from the group consisting of hexamethyldisiloxane, octamethyltrisiloxane, hexamethylcyclotrisiloxane, octamethylcyclotetrasiloxane, decamethylcyclopentasiloxane, tetramethyldisiloxane, trimethylcyclotrisiloxane, tetramethylcyclotetrasiloxane, pentamethylcyclopentasiloxane, divinyltetramethylsiloxane, trimethyltrivinylcyclosiloxane, and tetramethyltetravinylcyclotetrasiloxane.

DETAILED DESCRIPTION OF PREFERRED EMBODIMENTS

Preparation of the Inventive Particles and Silica Sols

The particles of the invention can be prepared, for example, by reacting silica sol with at least one first modifier comprising at least one alkoxysilane and with at least one second modifier selected from the group consisting of a halosilane, a siloxane, and mixtures thereof.

Contemplated as starting material for the silicon dioxide particles of the invention are dispersions of colloidal silicon dioxide or solvents. Use may be made of a colloidal silicon dioxide which has been prepared, for example, by the Stöber synthesis or from waterglass. Colloidal silicon dioxide for the purposes of the present invention means particles having an average diameter of 1 to 1000 nm, preferably of 5 to 150 nm. They may be present in dispersion in a liquid (silica sol). The particles are composed substantially—that is, preferably to an extent of at least 90%, more preferably to an extent of at least 95% or 99%—of silicon dioxide.

In the Stöber synthesis, alkoxysilanes, such as tetramethoxysilane, are hydrolyzed in the presence of acids or bases as catalyst, and by this means particles are constructed in a targeted way. The advantage of this process is that very narrow particle size distributions and any desired particle size between 5 and 500 nm can be achieved.

In the preparation of colloidal silica sol starting from waterglass, an aqueous solution of sodium silicate is deionized by means of an ion exchanger to form silica ($Si(OH)_4$). The silica formed is generally unstable and polymerizes directly to form small seed particles, from which the actual particles are then constructed. By appropriate setting of the operational conditions it is possible to produce narrow particle size distributions in the range of, for example, about 5 to 150 nm. The aqueous silica sols are stabilized generally with bases, as a result of which the acidic silica particles are negatively charged and repel one another. If, in the context of the present invention, a silica sol is used as starting material that comprises a base as a result, for example, of its preparation process, however, that base is preferably first of all removed.

Use may also be made of commercially available silicon dioxide particles, examples being Bindzil 40/130 and Bindzil 40/220 (available from Eka Chemicals); Levasil 200/40% (available from H.C. Starck); Nalco 2327. Nalco 1144. and Nalco 2329 (available from Nalco Company); NexSil 12 and NexSil 20 (available from Nyacol); Snowtex ST-40 and Snowtex ST-50 (available from Nissan Chemical American Corporation).

The process of the invention therefore preferably starts from a nanoscale colloidal silica sol. The pH of this sol is adjusted preferably to 5 or less, more preferably to 4 or less. In the case of a basic sol, this can be accomplished by adding acid or by using an acidic cation exchanger.

The reaction with the first and second modifiers may take place either successively or else simultaneously with a mixture of the first and second modifiers.

In the context of the process of the invention, at any desired point in time during the process, water is preferably removed from the silica sol, since substantial amounts of water in the reaction mixture mean that the reaction system as a whole is more polar. The removal of the water may take place, accordingly, before the reaction with the first modifier or before the reaction with the second modifier, or else on both occasions. Where a mixture of modifiers is used, the removal may take place even before the reaction with this mixture. Preferably the removal of water takes place before the reaction with a modifier or modifier mixture comprising halosilane and/or an organosilane.

For the purposes of the invention, the "removal of water" means the reduction of the water content of the system, based on the silicon dioxide content, to not more than 90%, preferably not more than 75%, 50%, 35%, 20% or 10% by weight. It is worth noting here that the water content of conventional, commercially available silicon dioxide sols is at least about 50% by weight, but usually about between 60% and 80% by weight (the water content, based on the silicon dioxide, is greater than 100% by weight in these cases). Following removal of water in accordance with the invention, therefore, the overall water content of the system may be below 15%, also preferably below 10%, or below 7.5% or below 5% by weight.

If, as preferably envisaged in the present process of the invention, water is removed from the reaction system, the possibility arises of operating with a relatively high content of, for example, up to 15%, more preferably up to 20%, in particular up to 25%, by weight, of the silica sol. Accordingly it is possible through the process of the invention to realize a significantly higher space-time yield.

It is known, moreover, that water promotes the agglomeration of silica particles. It is therefore preferred to remove water from the reaction system of the silica sol.

In one embodiment of the present invention, therefore, the process of the invention comprises the steps of
i. reacting colloidal silica sol with at least one first modifier comprising at least one alkoxysilane,
ii. reacting colloidal silica sol with at least one second modifier selected from a halosilane, a siloxane, and mixtures thereof, and
iii. removing water from the silica sol, in particular by azeotropic distillation.

The sequence of the individual process steps (1) to (3) that is envisaged here is not restricted and is variable. For instance, it is possible in principle, in the context of the present invention, in the case of a two-stage modification of the surface of a silica sol, to remove the water from the reaction system before the first surface modification or between the first and second surface modifications.

In one preferred embodiment of the process of the invention, however, the reaction of the colloidal silica sol takes place first of all with at least one first modifier comprising at least one alkoxysilane (process step (1)), before the removal of water from the silica sol (3), which is followed by the reaction with at least one second modifier selected from a halosilane, a siloxane, and mixtures thereof (process step (2)).

In the text below, the individual process steps (1) to (3) are described in more detail, and—as already remarked—the denotation/numbering of each of the process steps does not imply any restriction on the sequence of the process steps.

Process Step (1)

The modification of the particle surface in process step (1) may take place by the reaction of silica sols with alkoxysilanes of the general formula (I)

$$R^1_x Si(OR^2)_{4-x}, \quad \text{Formula (I)}$$

in which the radical $R^1$ is an optionally substituted $C_1$-$C_{18}$ alkyl radical and the radical $R^2$ may be selected from the group consisting of an optionally substituted $C_1$-$C_{18}$ alkyl radical, a carboxyl radical, an optionally substituted $C_2$-$C_{18}$ alkenyl radical, and an oxime radical.

It is notable that hydrolysis of the resultant SiOR groups may result in SiOH groups, to which, in turn, alkoxysilanes may undergo addition. Hence it is possible, wholly or partly, for layers to result that have Si(R)-x-O—Si(R)x linkages.

In the context of the present invention, the compounds of the general formula (I) are preferably selected from the group consisting of methyltrimethoxysilane, trimethylmethoxysilane, methylhydrodimethoxysilane, dimethyldimethoxysilane, ethyltrimethoxysilane, ethyltriacetoxysilane, propyltrimethoxysilane, diisopropyldimethoxysilane, diisobutyldimethoxysilane, chloropropyltrimethoxysilane, chloropropylmethyldimethoxysilane, chloroisobutylmethyldimethoxysilane, trifluoropropyltrimethoxysilane, trifluoropropylmethyldimethoxysilane, isobutyltrimethoxysilane, n-butyltrimethoxysilane, n-butylmethyldimethoxysilane, phenyltrimethoxysilane, phenyltrimethoxysilane, phenylmethyldimethoxysilane, triphenylsilanol, n-hexyltrimethoxysilane, n-octyltrimethoxysilane, isooctyltrimethoxysilane, decyltrimethoxysilane, hexadecyltrimethoxysilane, cyclohexylmethyldimethoxysilane, cyclohexylethyldimethoxysilane, dicyclopentyldimethoxysilane, tert-butylethyldimethoxysilane, tert-butylpropyldimethoxysilane, dicyclohexyldimethoxysilane, mercaptopropyltrimethoxysilane, mercaptopropylmethyldimethoxysilane, bis(triethoxysilylpropyl) disulfide, bis(triethoxysilylpropyl) tetrasulfide, aminopropyltrimethoxysilane, m-aminophenyltrimethoxysilane, aminopropylmethyldiethoxysilane, phenylaminopropyltrimethoxysilane, aminoethylaminopropyltrimethoxysilane, aminoethylaminopropylmethyldimethoxysilane, glycidyloxypropyltrimethoxysilane, glycidyloxypropylmethyldimethoxysilane, epoxycyclohexylethyltrimethoxysilane, γ-methacryloyloxypropyltriacetoxysilane, vinyltriacetoxysilane, vinyltrimethoxysilane, methylvinyldimethoxysilane, vinyldimethylmethoxysilane, divinyldimethoxysilane, vinyltris(2-methoxyethoxy)silane, hexenyltrimethoxysilane, γ-methacryloyloxypropyltrimethoxysilane, acryloyloxypropyltrimethoxysilane, vinylbenzylethylenediaminopropyltrimethoxysilane, vinylbenzylethylenediaminopropyltrimethoxysilane hydrochloride, allylethylenediaminepropyltrimethoxysilane, allyltrimethoxysilane, allylmethyldimethoxysilane, allyldimethylmethoxysilane, and hexenyltrimethoxysilane.

Particularly preferred in the context of the present invention are silanes of the general formula (I-1)

$$R^1 Si(OR^2)_3 \, (x=3) \quad \text{Formula (I-1)}$$

where the radicals $R^1$ and $R^2$ are as defined above.

Process step (1) is carried out preferably with the following conditions: For process step (1), the silica sol, if it has been given basic stabilization, is treated with a cation exchanger. The acidic silica sol is then reacted.

If the silane of formula (I-1) is sufficiently soluble in the silica sol, the reaction takes place preferably at room temperature within two hours. If the silane is not sufficiently soluble in the silica sol (discernible from spots of fat after 15 minutes of intense mixing), the mixture must be diluted with a water-miscible solvent. Particularly preferred for this purpose is isopropanol or 1-methoxy-2-propanol. The mixture with the silane can also be heated.

The preferred amount of silane can be calculated on the basis of the specific particle surface area $A_0$. It is preferred to use 1.5–6*μmol(silane)/g($SiO_2$)*$A_0$. The larger the particles, the smaller the specific surface area and the lower the required amount of silane. The specific surface area employed can be the surface according to the BET method or according to the method described below based on the particle size.

Under these conditions, the silane reacts completely with the particle surface, and so the loading with groups corresponds substantially to the stoichiometry employed.

Process Step (2)

The modification of the silica sol surface in process step (2) takes place, for example, by the reaction of the silica sol with a halosilane and/or a siloxane.

These halosilanes preferably have the general formula (II)

$$R^3_a H_b SiX_{4-a-b} \quad \text{Formula (II)}$$

in which each $R^3$, independently of any other, is selected from the group consisting of hydrocarbon radicals having 1 to 18 carbon atoms or organofunctional hydrocarbon radicals having 1 to 18 carbon atoms;

X, independently at each occurrence, is selected from the group consisting of fluorine, chlorine, bromine, and iodine;

a is 0, 1, 2 or 3;

b is 0 or 1; and a+b=1, 2 or 3.

The halosilanes which can be used for the process of the invention advantageously have the capacity to generate particles with the modification of type B. For this purpose, a is preferably 1-3. more preferably 2 or 3. It is particularly preferred to use a halosilane, more preferably a chlorosilane. The silanes may be functionalized, with polymerizable groups, for example, particularly with vinyl groups.

Particularly preferred in the context of the present invention are chlorosilanes of the general formula (II-1)

$$R^3_a H_b SiCl_{4-a-b}, \quad \text{Formula (II-1)}$$

where the radical $R^3$ and the indices a and b are as defined above.

Especially preferred in the context of the present invention are halosilanes of the general formula (II-2)

$$R^3_a H_{3-a} SiCl, \quad \text{Formula (II-2)}$$

where the radical $R^3$ and the index a are as defined above.

In the context of the present invention, the compounds of the general formula (II) are preferably selected from the group consisting of chlorotrimethylsilane, bromotrimethylsilane, iodotrimethylsilane, dichlorodimethylsilane, dichloromethylsilane, methyltrichlorosilane, chlorodimethylsilane, trichlorosilane, ethyltrichlorosilane, propyltrichlorosilane, phenyltrichlorosilane, dichlorodiphenylsilane, n-hexyltrichlorosilane, n-octyltrichlorosilane, chlorodimethyloctylsilane, chlorodimethyloctadecylsilane, vinyltrichlorosilane, dichloromethylvinylsilane, chlorodimethylvinylsilane, dichlorodivinylsilane, γ-methacryloyloxypropyldimethylchlorosilane, allyltrichlorosilane, allyldichloromethylsilane, and allylchlorodimethylsilane.

The siloxanes have the preferred general structure (III)

$$R^3_n SiO_{(4-n)/2} \quad \text{Formula (III)}$$

in which
each $R^3$, independently of any other, is selected from the group consisting of hydrocarbon radicals having 1 to 18 carbon atoms, organofunctional hydrocarbon radicals having 1 to 18 carbon atoms, a hydrogen atom, and an OH group; and n is a number between 2 and 3, inclusively.

Preferred in the context of the present invention are disiloxanes of the general formula (III-1)

$$R^3_3 SiOSiR^3_3, \quad \text{Formula (III-1)}$$

where the radical $R^3$ is as defined above, and two or more $R^3$s may each have a different definition.

Further preferred in the context of the present invention are cyclic siloxanes of the general formula (III-2)

$$(R^3_2 SiO)_n, \quad \text{Formula (III-2)}$$

where n is an integer, and two or more $R^3$s may each have a different definition.

Further preferred in the context of the present invention are polysiloxanes of the general formula (III-3)

$$R^3_3 SiO(R^3_2 SiO)_n SiR^3_3, \quad \text{Formula (III-3)}$$

where n is an integer, and two or more $R^3$s may each have a different definition.

In the context of the present invention, the compounds of the general formula (III) are preferably selected from the group consisting of alkyltrimethoxysilanes having 8 or more C atoms (e.g., octyltrimethoxysilane, isooctyltrimethoxysilane, hexadecyltrimethoxysilane, octadecyltrimethoxysilane, and methacryloyloxypropyltrimethoxysilane), hexamethyldisiloxane, octamethyltrisiloxane, hexamethylcyclotrisiloxane, octamethylcyclotetrasiloxane, decamethylcyclopentasiloxane, tetramethyldisiloxane, trimethylcyclotrisiloxane, tetramethylcyclotetrasiloxane, pentamethylcyclopentasiloxane, divinyltetramethylsiloxane, trimethyltrivinylcyclosiloxane, and tetramethyltetravinylcyclotetrasiloxane.

If the modification of the silica sol in process step (2) is carried out only with a siloxane and in particular without the simultaneous use of at least one halosilane, it is further preferred to use an acid additionally during the reaction. The reaction of silica sols with a halosilane and/or with a siloxane is based on the possibility of the siloxanes or alkoxysilanes formed in the hydrolysis or alcoholysis, respectively, being able to be cleaved again by means of acids and converted into more reactive products. If halosilanes, such as chlorotrimethylsilane, are used in aqueous media, then, in addition to the reaction with SiOH groups on the particle surface, hexamethyldisiloxane and hydrochloric acid are produced as well. The hydrochloric acid in turn may cleave Si—O—Si bonds in equilibrium and therefore return the hexamethyldisiloxane to the chlorotrimethylsilane. Consequently, it is possible to use a mixture of halosilanes and siloxanes, halosilane alone, or else a mixture of siloxanes with acid, such as hydrochloric acid.

As acid, use is made in this context of any desired Brønsted acid (as described, for example, in J. Huheey, Anorganische Chemie, Walter de Gruyter, Berlin, New York, 1988 p. 309f.). Since, however, many acids such as hydrochloric acid have a strongly corrosive effect with respect, for example, to the materials of the apparatus in which the process of the invention is carried out, their use is confined to corrosion-resistant systems. In accordance with the invention, this problem associated with the use of a Brønsted acid is preferably solved by using a Lewis acid in place of or in addition to the Brønsted acid. One possible Lewis acid in this content is aluminum chloride.

If a Brønsted acid or a Lewis acid is used in the context of the process of the invention, it is preferably neutralized or removed from the surface-modified silica sol after use.

Through the amount of the modifier in the second process step, the temperature of the reaction, and the duration of the reaction it is possible to control the properties of the resultant silica sols, such as the polarity and the redispersibility.

Process step (2) is carried out preferably with the following conditions: The reaction is preferably carried out with chlorosilanes or with a mixture of chlorosilanes and siloxanes. As far as the siloxanes are concerned, the disiloxanes in particular are preferred, since excess disiloxanes can be separated from the mixture, after the reaction, by distillation.

The reaction is carried out preferably in an organic medium, with a water content of between 1% and 10%. The preferred reaction temperature is a little below the boiling temperature of the mixture. When 1 mmol (chlorosilane)/g ($SiO_2$) is used, a complete reaction can be achieved at 70° C. within 2 hours.

Depending on the amount of siloxane and halosilane, a degree of coverage of up to 90% of the SiOH groups on the surface is achieved.

Colloidal silica typically has about 4.6 SiOH groups per $nm^2$.

Process Step (3)

The water can be removed from the silica sol by means, for example, of extraction with a phase separation, by distillation, by azeotropic distillation or by a membrane technique.

In one preferred embodiment of the process of the invention the water is removed by azeotropic distillation with an organic solvent.

The azeotropic distillation affords the advantage that the water can be removed from the silica sol system without having to consider the suitability of the organic solvent for phase separation. Since azeotropic distillation is generally accomplished successfully with virtually all organic solvents with which water forms an azeotrope, the azeotropic distillation increases the selection possibilities for the organic solvent, resulting overall in a process with greater flexibility.

The organic solvent which is used for the azeotropic removal of water from the silica sol is not subject to any particular restriction, and any desired solvent can be used that forms an azeotrope with water. Preference is given in this context to the use of a solvent which leads to a water-miscible system of silica sol and solvent. Preferred solvents, therefore, are those which can be mixed with water substantially completely, also using surface-active agents.

Suitable solvents for the azeotropic distillation may be selected, for example, from the group consisting of alcohols, such as methanol, ethanol, n-propanol, isopropanol, pentanols, octanols, and cyclohexanol; glycols, such as ethylene glycol and diethylene glycol; ethers, glycol ethers and propylene glycol ethers, such as diethyl ether, dibutyl ether, anisole, 1,4-dioxane, 1,3-dioxane, 1,3-dioxolane, tetrahydrofuran, 1-methoxy-2-propanol, 1-methoxy-1-propanol, 2-methoxyethanol, 1-ethoxy-2-propanol, mono-, di-, tri-, and polyethylene glycol ethers; ketones and aldehydes, such as acetone, butanone, and cyclohexanone; esters, such as acetic esters and glycol esters; amides and other nitrogen-containing solvents, such as dimethylformamide and nitrobenzene, piperidine, N-methylpiperidine, and acetonitrile; sulfur-containing solvents, such as dimethyl sulfoxide; halogenated hydrocarbons, such as dichloromethane, chloroform, carbon tetrachloride, tri- and tetrachloroethane, 1,2-dichloroethane, hydrochlorofluorocarbons; hydrocarbons, such as pentane, hexane, heptane, benzines, petroleum ether, cyclohexane, methylcyclohexane, decalin, terpenes, benzene, toluene, and xylenes; and the like. Especially preferred is isopropanol.

The process of the invention may further comprise other, optional process steps, an example being the removal of volatile constituents, such as of excess silanes, which is preferably accomplished by distillation.

In a further preferred embodiment of the present invention, the modification of the silica sols is carried out at an acidic pH, though it is not possible to specify further the precise acidic pH, since the reaction of the invention is carried out in an organic solvent.

The present invention relates, furthermore, to the silica sols obtainable by the process described above.

The present invention additionally provides for the use of the silica sols of the invention and of the silica sols obtainable by the process described above. The dispersion of the invention, or the redispersible powder obtained from the dispersion by removal of the solvent, can be incorporated into a wide variety of base polymers and can modify or improve their physical and, in particular, their mechanical properties. In the context of the invention, a large number of known polymers may be used as base polymers. For example, by means of the systems of the invention, thermoplastic or thermoset plastics may be modified. Mention may be made, by way of example, of polyolefins, polycarbonates, polyamides, polyimides, polyacrylates, polymethacrylates, polyetherketones, polysulfones, polyurethanes, polyureas, epoxy resins, and polyester resins. Examples of elastomers that can be modified include natural rubber, butylene rubbers, acrylate rubbers, styrene-butadiene rubber (SBR), optionally hydrogenated nitrile-butadiene rubbers, polysiloxanes (silicones), etc. With many of these groups of substances it is a particular advantage to incorporate the nanoparticles of the invention in the form of a redispersible powder, since their introduction via solvent is deleterious and is associated with high cost and complexity.

The nanoscale silicon dioxide of the invention can with particular advantage also be incorporated into polymers or resins having a low boiling point, such as methyl methacrylate (MMA), for example.

Particles produced in accordance with the invention may likewise be used for modifying plasticizers such as, for example, adipates and phthalates. With these plasticizers they form stable dispersions of low viscosity.

The polymeric or polymerizable mixtures comprising particles produced in accordance with the invention constitute stable and therefore storable dispersions and have good flow properties (low viscosity, low pseudoplasticity). They are therefore suitable, for example, for producing dental formulations which are applied, for example, from a static mixer and must therefore not have excessive processing viscosities. With particular preference they can be used with dental formulations based on silicones. Another possible territory of application is in the modification of LSRs (liquid silicone rubber), which are generally processed by injection molding and for which, therefore, a low processing viscosity is a great advantage. In accordance with the invention, in the case of LSRs, a high filler content and hence good mechanical properties on the part of the cured end product can be achieved, without the processing possibilities suffering as a result of an excessive viscosity.

The invention makes it possible in principle to prepare polymerizable mixtures which on the basis of their low viscosity have good processing properties and, in the form of cured polymer, have improved properties brought about by a high filler content, especially mechanical properties, improved thermal conductivity, and the like.

From the silica sols obtained in this way and also from the silica sols described before, it is possible, after removal of the solvent, to obtain powders, which can be redispersed in various media. In this context it has emerged, surprisingly, that the particle size distribution following dispersion corresponds substantially to the particle size distribution in the solvent, despite the agglomeration of the particles in the course of drying, since the stabilizing medium is absent. In the present case according to the invention, however, the agglomeration is substantially reversible, and so the particles can be converted back into a dispersion with a low energy cost and effort. The surface-modified silica sol may be dried, for example, by spray drying.

The subject matter according to the invention features a series of advantages. For instance, by varying the alkoxysilane for the first modification, the properties of the particles can be set independently of the halosilanes and/or the siloxanes of the second modification. Through the amount of halosilane and/or siloxane in the second modification, in turn, it is possible to influence the polarity of the resultant silica sol particles, since silica sol particles coated only with an alkoxysilane are generally relatively polar, while through the second modification the coating as a whole becomes more apolar again. Through a skillful combination of the nature and amount of the first and second modifications it is possible to produce particles which on a custom-tailored basis produce a stable dispersion in specified solvents. The process of the invention allows, so to speak, a modular chemistry for the targeted setting of polarity and, at the same time, a shielding of the surface.

Since the second modification is an equilibrium reaction, the fraction of apolar silyl groups on the surface can be adjusted in a targeted way via the amount of silane in the reaction.

The silica sols of the invention and silica sols obtainable by the process of the invention can be used for producing redispersible powders.

Through the use of the silica sols of the invention it is possible to improve the mechanical properties, particularly the tensile strength, the modulus of elasticity, the tear propagation resistance, the flexural modulus, and the impact strength in elastomers, composite materials, and thermoplastic materials. When the silica sols of the invention are used in the production, for example, of optical lenses, it is possible to achieve higher refractive indices. In addition, the gas barrier properties, the fire behavior, and the flow properties are improved through the silica sol dispersions of the invention.

Furthermore, the surface-modified silica sols obtained may be used in dispersion form for the production, for example, of composites (nanocomposites). Accordingly, the invention further provides the composites (nanocomposites) obtainable with the silica sols of the invention. These composites are advantageous because of their improved mechanical properties, examples being increased scratch resistance and abrasion resistance (tribology). This applies, for example, in respect of use in coating materials.

The present invention is described in more detail by the examples which follow, but which do not restrict the present invention.

EXAMPLES

Method of Particle Size Determination

The particle size may be accomplished in solution by means of dynamic light scattering (DLS) on an LB-550 Dynamic Light Scattering Particle Size Analyzer from Horiba at a concentration of not more than 10% by weight of particles, for which the dispersion ought to have not more than a dynamic viscosity of 3 mPas at 25° C. The particle size reported is the median (D50) of the particle size distribution.

In the solid material, the particle size can be determined by transmission electron microscopy. For this purpose, at least 100 particles are subjected to measurement, and a particle size distribution is formed.

Determination of the Surface Area

The surface area is calculated on the basis of the particle size. The assumption is made here that all of the particles have the same diameter corresponding to the median ($d_{50}$) of the particle size distribution, and have a spherical form.

The specific surface area ($nm^2/g$ (particle)) is given by:
$A_0 = 6/(\rho \times d_{50})$,
where $\rho$ is the density of the particles (density ($SiO_2$)=2.1 $g/cm^3$).

The number of groups, N, is given by:
$N = ([mol (reactive groups]/[mass of the particles]) \times 6.022 \times 10^{23}$ The ratio ($N/A_0$) gives the number of groups per unit surface area.

In the case of the reaction of alkoxysilanes it is possible to make the simplifying assumption that the silane used undergoes complete hydrolysis on the surface of the particles.

Comparative Examples

A basic colloidal silica sol (40% by weight $SiO_2$ in water; average particle size $d_{50}$ (determined by dynamic light scattering): 25 nm; stabilized with NaOH) was stirred over an acidic ion exchanger (Amberjet 1200H, available from Rohm & Haas) until a pH of 2 to 3 was reached. Following the removal of the ion exchanger by filtration, the acidic sol was stirred with various alkoxysilanes (see items 2 to 5 in Tables 1 and 2 below) for 2 hours. Example 1 was carried out without alkoxysilane and therefore served for comparison.

The sol was subsequently diluted with isopropanol and, with addition of further isopropanol, the mixture of solvent and water was distilled off under reduced pressure. The sol obtained was admixed, with stirring, with chlorotrimethylsilane and hexamethyldisiloxane. The mixture was stirred at 70° C. for two hours, then neutralized by addition of Amberjet 4400 OH, and the ion exchanger was removed by filtration.

Results

For the comparison of the properties of the particles with different alkoxysilanes (see items 2 to 5 in Tables 1 and 2) in the first coating, silica sols were dried in vacuo at 40° C. The resulting powders were redispersed in toluene, giving sols with a 10% by weight solids fraction. These sols were subjected to measurement by dynamic light scattering.

TABLE 1

| Example | Particle size $d_{50}$ [nm] | Span $(d_{90} - d_{10})/(d_{50})$ | Viscosity [mPas] |
|---|---|---|---|
| 1) No alkoxysilane | 696 | 4.0 | 20 |
| 2) Propyltrimethoxysilane | 30.3 | 0.7 | 0.9 |
| 3) Octyltrimethoxysilane | 28.0 | 0.7 | 0.7 |

Evaluation of Table 1 shows that, the closer the measured particle size to the original particle size and particle size distribution, the more suitable the particles for redispersion in toluene. From the results in Table 1 it is apparent that the alkoxysilane used in the first process step considerably improves the redispersibility of the particles in toluene. The viscosity of the dispersions as well is a measure of the compatibility of the particles with the matrix (solvent). In toluene, the particles reacted with alkoxysilane give rise to a considerably lower viscosity than the particles without alkoxysilane, i.e., their compatibility with toluene is better.

When different silica sols are transferred by solvent exchange into toluene and are subjected to measurement by means of DLS, the polarity of the particles can be gauged from a comparison with the original isopropanol sol.

TABLE 2

| Alkoxysilane | Particle size $d_{50}$ in isopropanol [nm] | Particle size $d_{50}$ in toluene [nm] |
|---|---|---|
| 4) Phenyltrimethoxysilane | 104 | 46 |
| 5) γ-Methacryloyloxypropyltrimethoxysilane | 44 | 4470 |

The compatibility of particles with solvents can be gauged from the particle size by dynamic light scattering. Particles which are not compatible with the solvent collect together and appear under dynamic light scattering to have a larger particle size. The closer the measured particle size is to the actual particle size, therefore, the fewer the particles that have collected together.

The results from Table 2 make it clear that the particles which have been reacted with the γ-methacryloyloxypropyltrimethoxysilane have better compatibility with the more polar solvent, isopropanol, than with the more apolar toluene. The polar γ-methacryloyloxypropyl group allows high compatibility with apolar solvents. These results show that the present invention is able to serve in the manner of a "modular chemistry" for the targeted attachment of desired molecules by means of silylation.

Procedure for Examples 1-3 (Table 1)

A basic colloidal silica sol (40% by weight $SiO_2$ in water, particle size (DLS) D50=25 nm, stabilized with NaOH) was stirred with acidic ion exchanger Amberjet 1200 H (Rohm & Haas) until a pH of 2 was reached. 100 parts of the sol were stirred with 0.24 mmol of the alkoxysilane/part (sol) for 2 hours (except in the case of Example 1). This was followed by dilution with 600 parts of isopropanol, and the sol was concentrated at 40-50° C. in vacuo to around 150 parts.

The sol was made up to 300 parts by weight by addition of isopropanol and then was admixed with a mixture of 4.4 parts of chlorotrimethylsilane and 13 parts of hexamethyldisiloxane and stirred at 70° C. for 2 hours. Following the removal of the heating, 25 parts of Amberjet 4400 OH (basic ion exchanger, Rohm & Haas) were added. Following a further hour of stirring, the ion exchanger was removed by filtration.

Procedure for Examples 4 and 5 (Table 2)

A basic colloidal silica sol (40% by weight $SiO_2$ in water, particle size (DLS) D50=25 nm, stabilized with NaOH) was stirred with acidic ion exchanger Amberjet 1200 H (Rohm & Haas) until a pH of 2 was reached. 100 parts of the sol were stirred with 0.24 mmol of the alkoxysilane/part (sol) for 2 hours. This was followed by dilution with 600 parts of isopropanol, and the sol was concentrated at 40-50° C. in vacuo to around 150 parts.

The sol was made up to 160 parts by weight by addition of isopropanol and then was admixed with a mixture of 4.4 parts of chlorotrimethylsilane and 13 parts of hexamethyldisiloxane and stirred at 70° C. for 2 hours. Following the removal of the heating, 25 parts of Amberjet 4400 OH (basic ion exchanger, Rohm & Haas) were added. Following a further hour of stirring, the ion exchanger was removed by filtration.

Example 6 (Table 3)

A basic colloidal silica sol (40% by weight $SiO_2$ in water, particle size (DLS) D50=25 nm, stabilized with NaOH) was stirred with acidic ion exchanger Amberjet 1200 H (Rohm & Haas) until a pH of 2 was reached. 100 parts of the sol were diluted with 50 parts of isopropanol, admixed with a mixture of 0.24 mmol of propyltrimethoxysilane/part (sol), 4.4 parts of chlorotrimethylsilane and 13 parts of hexamethyldisiloxane, and stirred at 70° C. for 2 hours. Following the removal of the heating, 25 parts of Amberjet 4400 OH (basic ion exchanger, Rohm & Haas) were added. After a further hour of stirring, the ion exchanger was removed by filtration. This was followed by dilution with 550 parts of isopropanol, and the sol was concentrated at 40-50° C. in vacuo to around 150 parts.

Example 7 (Table 3)

A basic colloidal silica sol (40% by weight $SiO_2$ in water, particle size (DLS) D50=25 nm, stabilized with NaOH) was stirred with acidic ion exchanger Amberjet 1200 H (Rohm & Haas) until a pH of 2 was reached. 100 parts of the sol were diluted with 200 parts of isopropanol, admixed with a mixture of 0.24 mmol of propyltrimethoxysilane/part (sol), 4.4 parts of chlorotrimethylsilane and 13 parts of hexamethyldisiloxane, and stirred at 70° C. for 2 hours. Following the removal of the heating, 25 parts of Amberjet 4400 OH (basic ion exchanger, Rohm & Haas) were added. After a further hour of stirring, the ion exchanger was removed by filtration. This was followed by dilution with 400 parts of isopropanol, and the sol was concentrated at 40-50° C. in vacuo to around 150 parts.

Example 8 (Table 3)

A basic colloidal silica sol (40% by weight $SiO_2$ in water, particle size (DLS) D50=25 nm, stabilized with NaOH) was stirred with acidic ion exchanger Amberjet 1200 H (Rohm & Haas) until a pH of 2 was reached. 100 parts of the sol were diluted with 600 parts of isopropanol, and the sol was concentrated at 40-50° C. in vacuo to around 150 parts.

The sol was admixed with a mixture of 0.24 mmol of propyltrimethoxysilane/part (sol), 4.4 parts of chlorotrimethylsilane and 13 parts of hexamethyldisiloxane, and stirred at 70° C. for 2 hours. Following the removal of the heating, 25 parts of Amberjet 4400 OH (basic ion exchanger, Rohm & Haas) were added. After a further hour of stirring, the ion exchanger was removed by filtration.

Comparison of Examples 6 to 8

The silica sols from Examples 6 to 8 were dried in vacuo at 40° C. and then redispersed in toluene, forming sols with 10% by weight.

| Example | Particle size $d_{50}$ [nm] | Span $(d_{90} - d_{10})/(d_{50})$ | Viscosity [mPas] |
|---|---|---|---|
| 6 | 3130 | 2.1 | 1.9 |
| 7 | 4220 | 1.1 | 2.8 |
| 8 | 91.9 | 1.8 | >20 |

The invention claimed is:

1. A surface-modified silicon dioxide particle or silica sol obtained by reacting aqueous silica sol with at least one first modifier comprising at least one alkoxysilane and with at least one second modifier selected from the group consisting of halosilane, siloxane, and mixtures thereof, with water being removed from the reaction by azeotropic distillation prior to reaction with the first or second modifier, wherein the reactions with the first and second modifiers are carried out successively.

2. The surface-modified silicon dioxide particle or silica sol of any claim 1, wherein the water content of the silica sol as a result of the removal of the water, based on the silicon dioxide content, is not more than 90%, by weight, and/or the total water content of the system is below 15%.

3. The surface-modified silicon dioxide particle or silica sol of claim 1, wherein the alkoxysilane is of the general formula (I–1) $R^1Si(OR^2)_3$ in which the radical $R^1$ is an unsubstituted, substituted or functionalized $C_1$-$C_{18}$ alkyl radical and the radical $R^2$ is selected from the group consisting of an unsubstituted, substituted or functionalized $C_1$-$C_{18}$ alkyl radical, a carboxyl radical, an unsubstituted, substituted $C_2$-$C_{18}$ alkenyl radical, and an oxime radical.

4. The surface-modified silicon dioxide particle or silica sol of claim 1, wherein the alkoxysilane is selected from the alkoxysilanes of the following group: methyltrimethoxysilane, trimethylmethoxysilane, methylhydrodimethoxysilane, dimethyldimethoxysilane, ethyltrimethoxysilane, ethyltriacetoxysilane, propyltrimethoxysilane, diisopropyldimethoxysilane, diisobutyldimethoxysilane, chloropropyltrimethoxysilane, chloropropylmethyldimethoxysilane, chloroisobutylmethyldimethoxysilane, trifluoropropyltrimethoxysilane, trifluoropropylmethyldimethoxysilane, isobutyltrimethoxysilane, n-butyltrimethoxysilane, n-butylmethyldimethoxysilane, phenyltrimethoxysilane, phenyltrimethoxysilane, phenylmethyldimethoxysilane, triphenylsilanol, n-hexyltrimethoxysilane, n-octyltrimethoxysilane, isooctyltrimethoxysilane, decyltrimethoxysilane, hexadecyltrimethoxysilane, cyclohexylmethyldimethoxysilane, cyclohexylethyldimethoxysilane, dicyclopentyldimethoxysilane, tert-butylethyldimethoxysilane, tert-butylpropyldimethoxysilane, dicyclohexyldimethoxysilane, mercaptopropyltrimethoxysilane, mercaptopropylmethyldimethoxysilane, bis(triethoxysilylpropyl) disulfide, bis(triethoxysilylpropyl) tetrasulfide, aminopropyltrimethoxysilane, m-aminophenyltrimethoxysilane, aminopropylmethyldiethoxysilane, phenylaminopropyltrimethoxysilane, aminoethylaminopropyltrimethoxysilane, aminoethylaminopropylmethyldimethoxysilane, glycidyloxypropyltrimethoxysilane, glycidyloxypropylmethyldimethoxysilane, epoxycyclohexylethyltrimethoxysilane, γ-methacryloyloxypropyltriacetoxysilane, vinyltriacetoxysilane, vinyltrimethoxysilane, methylvinyldimethoxysilane, vinyldimethylmethoxysilane, divinyldimethoxysilane, vinyltris(2-methoxyethoxy)silane, hexenyltrimethoxysilane, γ-methacryloyloxypropyltrimethoxysilane, acryloyloxypropyltrimethoxysilane, vinylbenzylethylenediaminopropyltrimethoxysilane, vinylbenzylethylenediaminopropyltrimethoxysilane hydrochloride, allylethylenediaminepropyltrimethoxysilane, allyltrimethoxysilane, allylmethyldimethoxysilane, allyldimethylmethoxysilane, and hexenyltrimethoxysilane.

5. The surface-modified silicon dioxide particle or silica sol of claim 1, wherein the halosilane is of the general formula (II) $R^3_aH_bSiX_{4-a-b}$ in which each $R^3$, independently of any other, is selected from the group consisting of hydrocarbon radicals having 1 to 18 carbon atoms and organofunctional hydrocarbon radicals having 1 to 18 carbon atoms; X, independently at each occurrence, is selected from the group consisting of fluorine, chlorine, bromine, and iodine;

a is 0, 1, 2 or 3;

b is 0 or 1; and a+b is 1, 2 or 3.

6. The surface-modified silicon dioxide particle or silica sol of claim 1, wherein the siloxane is of the general formula (III) $R^3{}_n SiO_{(4-n)/2}$ in which each $R^3$, independently of any other, is selected from the group consisting of hydrocarbon radicals having 1 to 18 carbon atoms, organofunctional hydrocarbon atoms having 1 to 18 carbon atoms, a hydrogen atom, and an OH group; and n is a number between 2 and 3 inclusive.

7. The surface-modified silicon dioxide particle or silica sol of claim 1, wherein the alkoxysilane is selected from propyltrimethoxysilane, phenyltrimethoxysilane, alkyltrimethoxysilanes having 8 or more C atoms, namely octyltrimethoxysilane, isooctyltrimethoxysilane, hexadecyltrimethoxysilane, octadecyltrimethoxysilane, and methacryloyloxypropyltrimethoxysilane, and the second modifier is composed of a mixture of chlorotrimethylsilane and hexamethyldisiloxane.

8. The surface-modified silicon dioxide particle or silica sol of claim 1, wherein the surface-modified silicon dioxide particle or silica sol is present in dried form.

9. The surface-modified silicon dioxide particle or silica sol of claim 8, wherein the surface-modified silicon dioxide particle or silica sol is redispersible after drying.

10. The surface-modified silicon dioxide particle or silica sol of claim 9, wherein the particle size distribution after dispersion corresponds substantially to the particle size distribution in the solvent.

11. A method of using a surface-modified silicon dioxide particle or silica sol as claimed in claim 1, in base polymers comprising incorporating a dispersion of the surface-modified silicon dioxide particle or silica sol or a redispersible powder obtained from the dispersion by removal of the solvent into a base polymer.

12. A polymer or polymerizable mixture comprising a surface-modified silicon dioxide particle or silica sol as claimed in claim 1.

13. A method of using a polymer as claimed in claim 12 for producing dental formulations.

14. A method of using a polymer as claimed in claim 13 for modifying liquid silicone rubber comprising providing silicone rubber and mixing it with the polymer.

15. A process for the preparation of surface-modified silicon dioxide particles or silica sol comprising, reacting aqueous silica sol with at least one first modifier comprising at least one alkoxysilane and at least one second modifier selected from the group consisting of halosilane, siloxane, and mixtures thereof, with water being removed prior to reaction with the first or second modifier by azeotropic distillation prior to reaction with the first or second modifier, wherein the reactions with the first and second modifiers are carried out successively.

16. The surface-modified silicon dioxide particle or silica sol of claim 5, wherein the halosilane is $R^3{}_a H_{3-a} SiCl$.

* * * * *